US008194872B2

(12) United States Patent
Buck et al.

(10) Patent No.: US 8,194,872 B2
(45) Date of Patent: Jun. 5, 2012

(54) MULTI-CHANNEL ADAPTIVE SPEECH SIGNAL PROCESSING SYSTEM WITH NOISE REDUCTION

(75) Inventors: Markus Buck, Biberbach (DE); Tim Haulick, Blaubeuren (DE); Phillip A. Hetherington, Port Moody (CA); Pierre Zakarauskas, Vancouver (CA)

(73) Assignee: Nuance Communications, Inc., Burlington, MA (US)

( * ) Notice: Subject to any disclaimer, the term of this patent is extended or adjusted under 35 U.S.C. 154(b) by 1229 days.

(21) Appl. No.: 11/234,837

(22) Filed: Sep. 23, 2005

(65) Prior Publication Data

US 2006/0222184 A1 Oct. 5, 2006

(30) Foreign Application Priority Data

Sep. 23, 2004 (EP) .................................... 04022677

(51) Int. Cl.
*A61F 11/06* (2006.01)
*H04B 15/00* (2006.01)
*H04R 1/40* (2006.01)

(52) U.S. Cl. ....................... 381/71.11; 381/94.1; 381/97

(58) Field of Classification Search ............... 381/71.11, 381/92, 94.1, 94.8, 94.5; 704/226
See application file for complete search history.

(56) References Cited

U.S. PATENT DOCUMENTS

| | | | | |
|---|---|---|---|---|
| 6,449,586 | B1 | 9/2002 | Hoshuyama | 702/190 |
| 2003/0108214 | A1* | 6/2003 | Brennan et al. | 381/94.7 |
| 2004/0161121 | A1* | 8/2004 | Chol et al. | 381/92 |

FOREIGN PATENT DOCUMENTS

| | | | |
|---|---|---|---|
| DE | 43 30 243 A1 | 3/1993 | |
| DE | 199 34 724 A1 | 4/2001 | |
| JP | 2000-047699 | 2/2000 | |
| JP | 2000-181498 | 6/2000 | |
| JP | 2003-0271191 | 9/2003 | |
| WO | WO 01/10169 A1 | 2/2001 | |

OTHER PUBLICATIONS

Herbordt, Wolfgang et al., "Adaptive Beamforming for Audio Signal Acquisition", Adaptive Signal Processing, Applications to Real-World Problems, J. Benesty et al. (Eds.), copyright 2003, Chapter 6, pp. 155-194.

(Continued)

*Primary Examiner* — Devona Faulk
*Assistant Examiner* — George Monikang
(74) *Attorney, Agent, or Firm* — Sunstein Kann Murphy & Timbers LLP

(57) ABSTRACT

An adaptive signal processing system eliminates noise from input signals while retaining desired signal content, such as speech. The resulting low noise output signal delivers improved clarity and intelligibility. The low noise output signal also improves the performance of subsequent signal processing systems, including speech recognition systems. An adaptive beamformer in the signal processing system consistently updates beamforming signal weights in response to changing microphone signal conditions. The adaptive weights emphasize the contribution of high energy microphone signals to the beamformed output signal. In addition, adaptive noise cancellation logic removes residual noise from the beamformed output signal based on a noise estimate derived from the microphone input signals.

24 Claims, 6 Drawing Sheets

OTHER PUBLICATIONS

Herbordt, W. et al., "Analysis of Blocking Matrices for Generalized Sidelobe Cancellers for non-Stationary Broadband Signals", *Student Forum of Int. Conference on Acoustics, Speech and Signal Processing*, May 2002, retrieved from the Internet at: <URL:http://www.int.de/LMS/publications/web/Int2002_007.pdf>, 4 pages.

Herbordt, Wolfgang et al., "Frequency-Domain Integration of Acoustic Echo Cancellation and a Generalized Sidelobe Canceller with Improved Robustness", *European Translations on Telecommunications*, vol. 13, No. 2, Jun. 2002, retrieved from the Internet at: <URL:http://www.Int.de/LMS/publications/web/Int2002_006>.pdf, pp. 1-10.

Hoshuyana, Osamu et al., "A Robust Adaptive Beamformer for Microphone Arrays with a Blocking Matrix Using Constrained Adaptive Filters", *IEEE Transactions on Signal Processing*, vol. 47, No. 10, 1999, pp. 2677-2684.

"Microphone Arrays—Signal Processing Techniques and Applications", M. Brandstein et al. (Eds.), copyright Springer-Verlag 2001, pp. 3-106 and 229-349.

Gannot, Sharon et al, "Signal Enhancement Using Beamforming and Nonstationarity With Applications to Speech", *IEEE Transactions on Signal Processing*, vol. 49, No. 8, 2001, pp. 1614-1626.

Griffiths, Lloyd J. et al, "An Alternative Approach to Linearly Constrained Adaptive Beamforming", *IEEE Transactions on Antennas and Propagation*, vol. AP-30, No. 1, 1982, pp. 27-34.

McCowan, Iain A. et al, "Adaptive Parameter Compensation for Robust Hands-Free Speech Recognition Using a Dual Beamforming Microphone Array", *Proceeding of 2001 International Symposium on Intelligent Multimedia, Video and Speech Processing*, 2001, pp. 547-550.

Oh, Stephen et al, "Hands-Free Voice Communication in an Automobile With a Microphone Array", *IEEE Digital Signal Processing*, vol. 5, 1992, pp. I-281 to I-284.

Van Veen, Barry D. et al, "Beamforming: A Versatile Approach to Spatial Filtering", *IEEE ASSP Magazine*, 1988, pp. 4-24.

* cited by examiner

MULTI-CHANNEL ADAPTIVE SPEECH SIGNAL PROCESSING SYSTEM WITH NOISE REDUCTION

PRIORITY CLAIM

This application claims the benefit of priority from European Patent Application No. 04022677.1, filed Sep. 23, 2004, which is incorporated herein by reference.

BACKGROUND OF THE INVENTION

1. Technical Field

This invention relates to signal processing systems. In particular, this invention relates to multi-channel speech signal processing using adaptive beamforming.

2. Related Art

Speech signal processing systems often operate in noisy background environments. For example, a hands-free voice command or communication system in an automobile may operate in a background environment which includes significant levels of wind or road noise, passenger noise, or noise from other sources. Noisy background environments result in poor signal-to-noise ratio (SNR), masking, distortion, corruption of signals, and other detrimental effects on signals. As a result, noisy background environments reduce the intelligibility and clarity of speech signals and reduce speech recognition accuracy.

Past attempts to improve signal quality in noisy background environments relied on multi-channel systems, such as systems including microphone arrays. Multi-channel systems primarily employ a General Sidelobe Canceller (GSC) which processes the speech signal along two signal paths. The first signal path suppresses the unwanted noise. The second signal path employs a non-adaptive (i.e., fixed) beamformer that synchronizes the signal of each microphone in the array. The synchronization is based on the limiting assumption that the microphone signals differ only by their time delays. Reliance on a fixed beamformer renders such systems susceptible to potentially wide variations in energy levels at each microphone in the array and the differences in SNR among the microphone signals.

In many practical applications, the SNR of each microphone signal of an array differs from the SNR of every other microphone signal obtained from the array. Under such conditions, the fixed beamformer may actually reduce performance of the noise reduction signal processing system. In particular, microphone signals with low SNR may contribute excessive noise to the beamformed output signal. Thus, past GSC implementations did not provide a consistently reliable mechanism for reducing noise, and do not provide speech command or communication systems with a consistently noise free signal.

Therefore, a need exists for an improved noise reduction signal processing system.

SUMMARY

This invention provides improved speech signal clarity and intelligibility. The improved speech signal enhances communication and improves downstream processing system performance across a wide range of applications, including speech detection and recognition. The improved speech signal results from substantially reducing noise, while retaining desired signal components.

A signal processing system generates the improved speech signal on a noise reduced signal output. The signal processing system includes multiple microphone signal inputs on which the processing system receives microphone signals. Time delay compensation logic time aligns the microphone signals and provides the time aligned signals to noise reference logic and to an adaptive beamformer.

The noise reference logic generates noise reference signals based on the time aligned microphone signals. The noise reference signals are provided to adaptive noise cancellation logic. The adaptive noise cancellation logic produces a noise estimate from the noise reference signals.

The adaptive beamformer applies adaptive real-valued weights to the time aligned microphone signals. The adaptive beamformer repeatedly recalculates and updates the weights. The updates may occur in response to temporal changes in noise power, speech amplitude, or other signal variations. Based upon the adapting weights, the adaptive beamformer combines the time aligned microphone signals into a beamformed output signal. Summing logic subtracts the noise estimate from the beamformed output signal. A low noise output signal results.

The signal processing system may include adaptive self-calibration logic connected to the time delay compensation logic. The adaptive self-calibration logic matches phase, amplitude, or other signal characteristics among the time aligned microphone signals. Alternatively or additionally, the signal processing system may include adaptation control logic connected to any combination of the adaptive self-calibration logic, adaptive beamformer, noise cancellation logic, and adaptive noise cancellation logic. The adaptation control logic initiates adaptation based on SNR, speech signal detection, speech signal energy level, acoustic signal direction, or other signal characteristics.

Other systems, methods, features and advantages of the invention will be, or will become, apparent to one with skill in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

Figure 1:
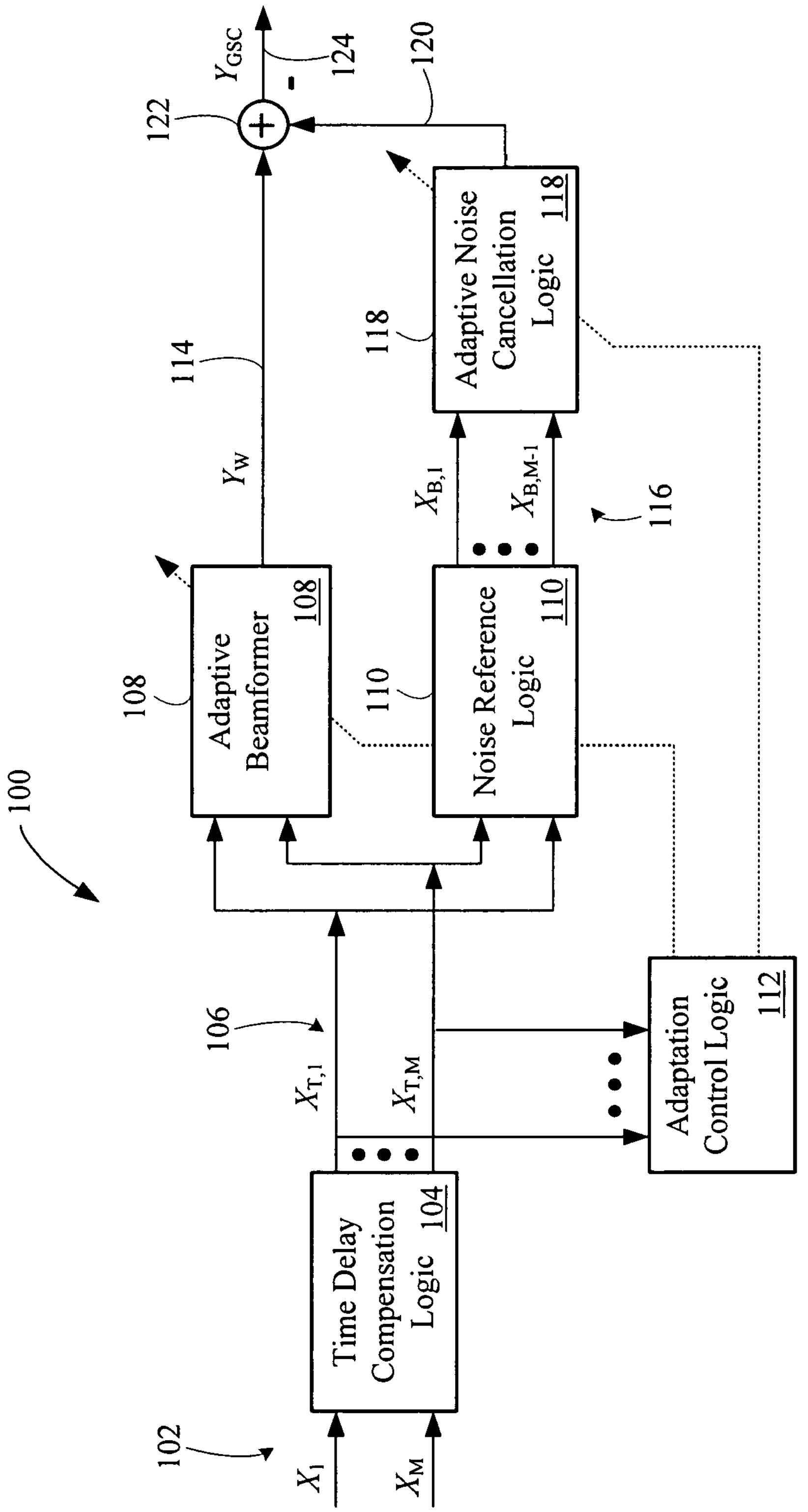
FIG. 1 shows a multi-channel adaptive signal processing system

FIG. 1 shows a multi-channel adaptive speech processing system 100. The processing system 100 reduces noise originally present in one or more input signals. A low noise output signal results.

The processing system 100 includes microphone signal inputs 102. The microphone signal inputs 102 communicate microphone signals $X_1$ to $X_M$ to time delay compensation logic 104. The microphone signals may be provided to the processing system 100 in the frequency domain and in sub-bands, denoted as $X_1(n,k)$ to $X_M(n,k)$, where the index 'M' denotes the number of microphones, 'n' is a frequency bin index, and 'k' is a time index. However, the processing system 100 may instead process the microphone signals in the time domain, a combination of the time domain and frequency domain, or in the frequency domain.

The time delay compensation logic 104 generates time aligned microphone signals $X_{T,1}$ to $X_{T,M}$ on time delay compensated microphone signal outputs 106. The time delay compensated microphone signal outputs 106 connect to an adaptive beamformer 108, noise reference logic 110, and adaptation control logic 112. The adaptation control logic 112 connects to any combination of the adaptive beamformer 108, the noise reference logic 110, and the adaptive noise cancellation logic 118.

The adaptive beamformer 108 combines the time aligned microphone signals $X_{T,1}$ to $X_{T,M}$ into a beamformed signal $Y_w$ provided on a beamformed signal output 114. The noise reference logic 110 provides noise reference signals $X_{B,1}$ to $X_{B,M}$ on noise reference signal outputs 116 to the adaptive noise cancellation logic 118. The adaptive noise cancellation logic 118 produces a noise estimate on the adaptive noise cancellation output 120.

The beamformed signal output 114 and adaptive noise cancellation output 120 connect to summing logic 122. The summing logic subtracts the noise estimate from the beamformed signal to generate the low noise output signal $Y_{GSC}$. The summing logic 122 provides $Y_{GSC}$ on the noise reduced signal output 124.

The time delay compensation logic 104 compensates for time delays between the microphone signals. A time delay in the microphone signals may arise when the microphones have different acoustic distances from the source of the speech signal. The microphones may have different acoustic distances from the source of the speech signal when the microphones point in different directions, are placed in different locations, or vary in another physical or electrical characteristic. The time delay compensation logic 104 compensates for the time delay by synchronizing the microphone signals. The time delay compensation logic 104 generates time aligned microphone signals $X_{T,1}$ to $X_{T,M}$ on the time delay compensated signal outputs 106.

The adaptive beamformer 108 applies weights $A_m(n)$ to the time aligned microphone signals. The weights may be real-valued weights. One step in determining the weights is to model the time aligned microphone signals $X_{T,1}$ to $X_{T,M}$ as including a signal component $S_m(n,k)$ and a noise component $N_m(n,k)$:

$$X_{T,m}(n,k)=S_m(n,k)+N_m(n,k)$$

The signal component may be modelled with positive scaling factors $\alpha_m$ as shown below:

$$S_m(n,k)=\alpha_m(n)S(n,k).$$

The noise components may be assumed orthogonal to one other and may have powers $\epsilon$ which differ as a function off $\beta_m$, a positive real-valued number:

$$\epsilon\{N_m(n,k)N_1(n,k)\}=0 \text{ form } m\neq 1$$

$$\epsilon\{|N_m(n,k)|^2\}=\beta_m^2(n)\epsilon\{|N(n,k)|^2\}$$

Based on the above signal and noise component models, the adaptive beamformer 108 may calculate the weights as:

$$\tilde{A}_m(n)=\frac{\alpha_m(n)}{\beta_m^2(n)}.$$

The adaptive beamformer 108 may normalize the weights as shown below. Normalization provides a unity response for the desired signal components.

$$A_m(n)=\frac{\tilde{A}_m(n)}{\sum_{l=1}^{M}\tilde{A}_l(n)}.$$

The adaptive weights $A_m(n)$ emphasize the contribution of the high energy microphone signals from each frequency band to the beamformed output signal. In practical applications, $\alpha_m(n)$ and $\beta_m(n)$ are time dependent. The adaptive beamformer 108 may repeatedly recalculate $A_m(n)$ in response to temporal changes in signal characteristics, such as the SNR, direction, or energy as noted above. The adaptive beamformer 108 may track the temporal changes by estimating the noise power $\epsilon\{|N_m(n,k)|^2\}$, by determining ratios of speech amplitude between different microphone signals, or in other manners.

The adaptive beamformer 108 applies the weights $A_m(n)$ to each time aligned microphone signal 'm' in each sub-band 'n'. The beamformed signal $Y_W$ provides intermediate results in each sub-band which will lead to the low noise output signal $Y_{GSC}$:

$$Y_w(n,k)=\sum_{m=1}^{M}A_m(n)X_{T,m}(n,k).$$

The noise reference logic 110 generates noise reference signals $X_{B,1}$ to $X_{B,M-1}$ based on the time aligned microphone signals. The noise reference logic 110 may be implemented with a blocking matrix, and may be adaptive. The blocking matrix may be a Walsh-Hadamard, Griffiths-Jim, or other type of blocking matrix. In other implementations, the noise reference logic 110 may determine the noise reference signals by subtracting adjacent time aligned microphone signals.

The noise reference logic 110 projects the time delay compensated microphone signals $X_{T,1}$ to $X_{T,M}$ onto the noise plane. The noise reference logic 110 thereby determines the noise reference signals $X_{B,1}$ to $X_{B,M-1}$. In other words, the noise reference logic 110 maps complex valued microphone signals to the noise reference signals, which are elements of the noise plane in noise space.

The noise reference signals $X_{B,1}$ to $X_{B,M-1}$ substantially eliminate what would ordinarily be the desired signal components in the microphone signals. For example, the noise reference signals $X_{B,1}$ to $X_{B,M-1}$ may substantially eliminate speech signal components. The noise reference signals $X_{B,1}$ to $X_{B,M-1}$ thereby provide a representation of the noise in the microphone input signals.

The noise reference signal outputs 116 connect to the adaptive noise cancellation logic 118. The adaptive noise cancellation logic 118 determines a noise estimate based on the noise reference signals $X_{B,1}$ to $X_{B,M-1}$ and adaptive complex-valued filters $H_{GSC,m}(n,k)$. The complex-valued filters may adapt to minimize the power in each sub-band of the low noise output signal: $\epsilon\{|Y_{GSC,m}(n,k)|^2\}$. Because the noise reference signals substantially eliminate the desired signal components, the residual noise in the beamformed output signal $Y_W$ is reduced and SNR is further increased in the low noise output signal $Y_{GSC}$.

To adapt the complex valued filters $H_{GSC,m}(n,k)$, the adaptive noise cancellation logic 118 may apply an adaptation algorithm such as the Normalized Least-Mean Square (NLMS) algorithm:

$$Y_{GSC}(n,k) = Y_w(n,k) - \sum_{m=1}^{M-1} X_{B,m}(n,k)H_{GSC,m}(n,k)$$

$$H_{GSC,m}(n,k+1) = H_{GSC,m}(n,k) + \frac{\beta_{GSC}(n,k)}{\sum_{l=1}^{M-1} |X_{B,l}(n,k)|^2} Y_{GSC,m}(n,k)X^*_{B,m}(n,k).$$

In the equation above, the asterisk denotes the complex conjugate of the noise reference signals. Thus, the adaptive noise cancellation logic uses the noise reference signals $X_{B,1}$ to $X_{B,M-1}$ and the complex valued filters $H_{GSC,m}(n,k)$ to generate the noise estimate. The noise estimate, subtracted from the beamformed output signal $Y_W$ yields the low noise output signal $Y_{GSC}$.

The summing logic 122 subtracts the noise estimate from the beamformed signal $Y_W$ to produce the low noise output signal $Y_{GSC}$ on the noise reduced signal output 124:

$$Y_{GSC}(n,k) = Y_w(n,k) - \sum_{m=1}^{M-1} X_{B,m}(n,k)H_{GSC,m}(n,k).$$

In the equation above, the summation represents the noise estimate determined by the adaptive noise cancellation logic 118. Removing noise from the beamformed signal $Y_W$ yields an increase in SNR of the output signal $Y_{GSC}$. The low noise output signal $Y_{GSC}$ enhances speech acquisition and subsequent speech processing, including speech recognition.

The adaptation control logic 112 may control adaptation of any combination of the adaptive beamformer 108, the noise reference logic 110, the adaptive noise cancellation logic 118, or the self-calibration logic 202. The adaptation control logic 112 controls adaptation step size. The step size may be based on the SNR of the microphone input signals (e.g. the instantaneous SNR), the detection of a speech signal in the microphone input signals, the speech signal energy level, the acoustic signal direction, or other signal characteristics.

The step size may be larger (and adaptation faster) when the SNR is high and/or when the desired signal comes from an expected direction (e.g., the direction of the driver in an automobile). The step size may be larger when the energy of a desired signal component (e.g., speech) exceeds background noise by a threshold. The threshold may be 5-12 db above the background noise, 7-8 db above the background noise, or may be set at another value. Signal energy 7-8 db (or more) above the background noise is a strong indicator that the desired signal component (e.g., speech) is present.

Adaptation of the weights in the adaptive beamformer 108 may give rise to an adaptation of the noise reference logic 110 and/or adaptive noise cancellation logic 118. Thus, the adaptation control logic 112 may adapt the noise reference logic 110 and/or the adaptive noise cancellation logic 118 in response to beamformer adaptation. The adaptive beamformer 108 may adapt when the energy of desired signal content (e.g., speech) exceeds the background noise by a threshold. Furthermore, the adaptation control logic 112 may adapt the noise cancellation logic 118 when noise is present and desired signal content (e.g., speech) is substantially absent or under a threshold.

Figure 2:
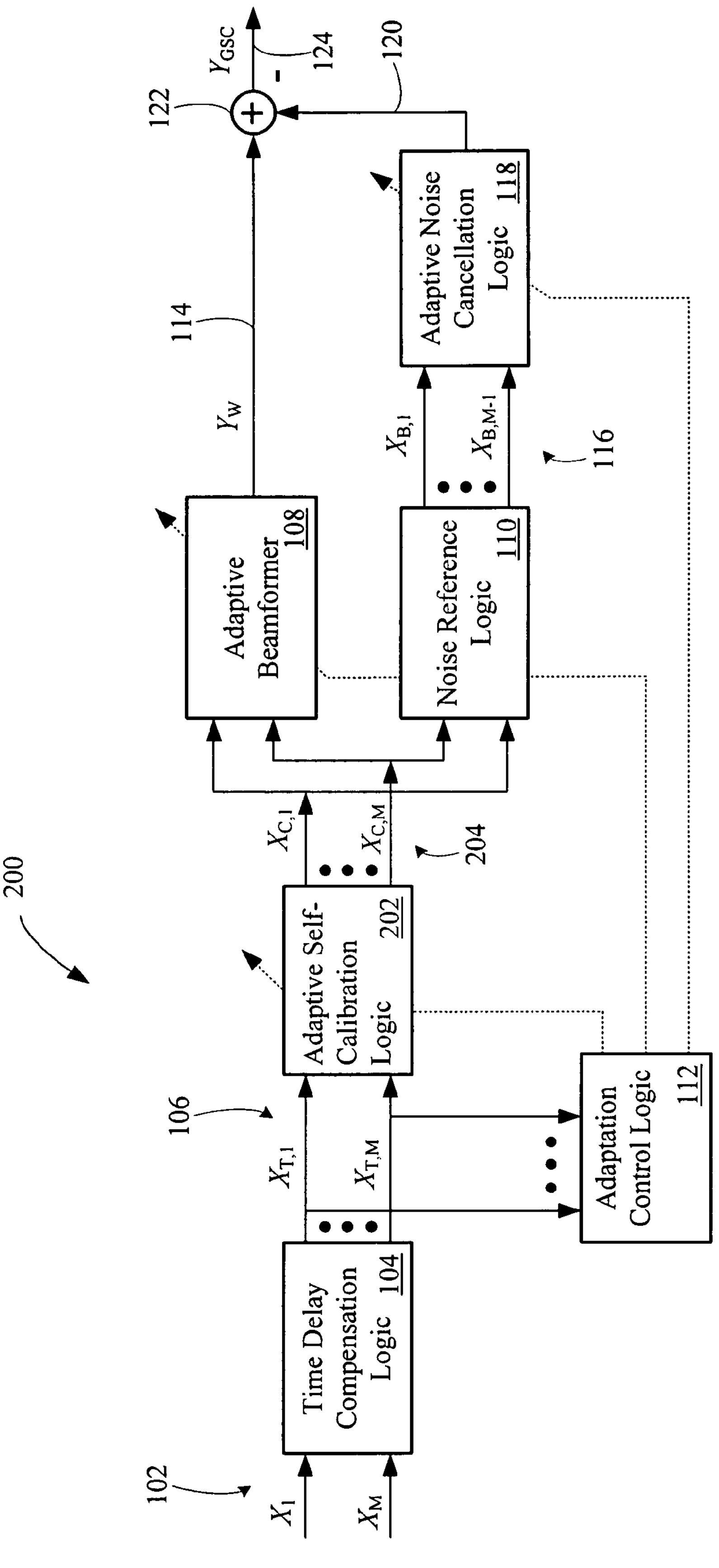
FIG. 2 shows a multi-channel adaptive signal processing system including adaptive self-calibration logic.

FIG. 2 shows a multi-channel adaptive speech processing system 200 including adaptive self-calibration logic 202. The adaptive self-calibration logic 202 minimizes mismatches in the time aligned microphone signals $X_{T,1}$ to $X_{T,M}$ provided by the time delay compensation logic 104. In particular, the adaptive self-calibrating logic 202 minimizes mismatches in phase, amplitude, or other signal characteristics of the time aligned microphone signals $X_{T,1}$ to $X_{T,M}$. Thus, in addition to time delay compensation, the processing system 200 employs the self-calibration logic 202 to match microphone signal frequency characteristics prior to combining the microphone signals in the adaptive beamformer 108.

The adaptive self-calibration logic 202 may use self-calibration filters $H_{C,m}(n,k)$. The self-calibration filters may determine the time aligned microphone signals $X_{T,1}$ to $X_{T,M}$ according to:

$$X_{C,m}(n,k)=X_{T,m}(n,k)H_{C,m}(n,k)$$

To facilitate filter adaptation, the adaptive self-calibration logic 202 may determine error signals $E_{C,m}(n,k)$:

$$E_{C,m}(n,k) = \frac{1}{M}\sum_{l=1}^{M} X_{C,l}(n,k) - X_{C,m}(n,k)$$

The adaptive self-calibration logic 202 may employ the error signals $E_{C,m}(n,k)$ in conjunction with an adaptation technique, such as the NLMS technique, which minimizes the power of the error signals $\epsilon\{|E_{C,m}(n,k)^2|\}$ as shown below:

$$\tilde{H}_{C,m}(n,k+1) = \tilde{H}_{C,m}(n,k) + \frac{\beta_C(n,k)}{|X_{T,m}(n,k)|^2} E_{C,m}(n,k)X^*_{T,m}(n,k).$$

The adaptive self-calibration logic 202 may rescale the filters to obtain a unity mean response:

$$H_{C,m}(n,k) = \tilde{H}_{C,m}(n,k) - \frac{1}{M}\sum_{l=1}^{M}\tilde{H}_{C,l}(n,k) + 1 \text{ with} \left(\frac{1}{M}\sum_{m=1}^{M} H_{C,m}(n,k) \overset{!}{=} 1\right).$$

Multiple microphones in an array, even microphones of the same type from the same manufacturer, may differ in sensitivity, frequency response, or other characteristics. The self-calibration logic 202 compensates for differences in microphone characteristics. The self-calibration logic 202 provides a long term matching of phase and amplitude characteristics among the microphones in the array. Thus, the self-calibration logic 202 may compensate for a microphone which is consistently more sensitive than another microphone and/or may compensate for a microphone with a different phase response than another microphone in the array. The adaptive self-calibration logic 202 generates self-calibrated time aligned microphone signals $X_{C,1}$ to $X_{C,M}$ on the self-calibrated time delay compensated signal outputs 204. The adaptive beamformer 108 and the noise reference logic 110 process the time aligned microphone signals.

Figure 3:
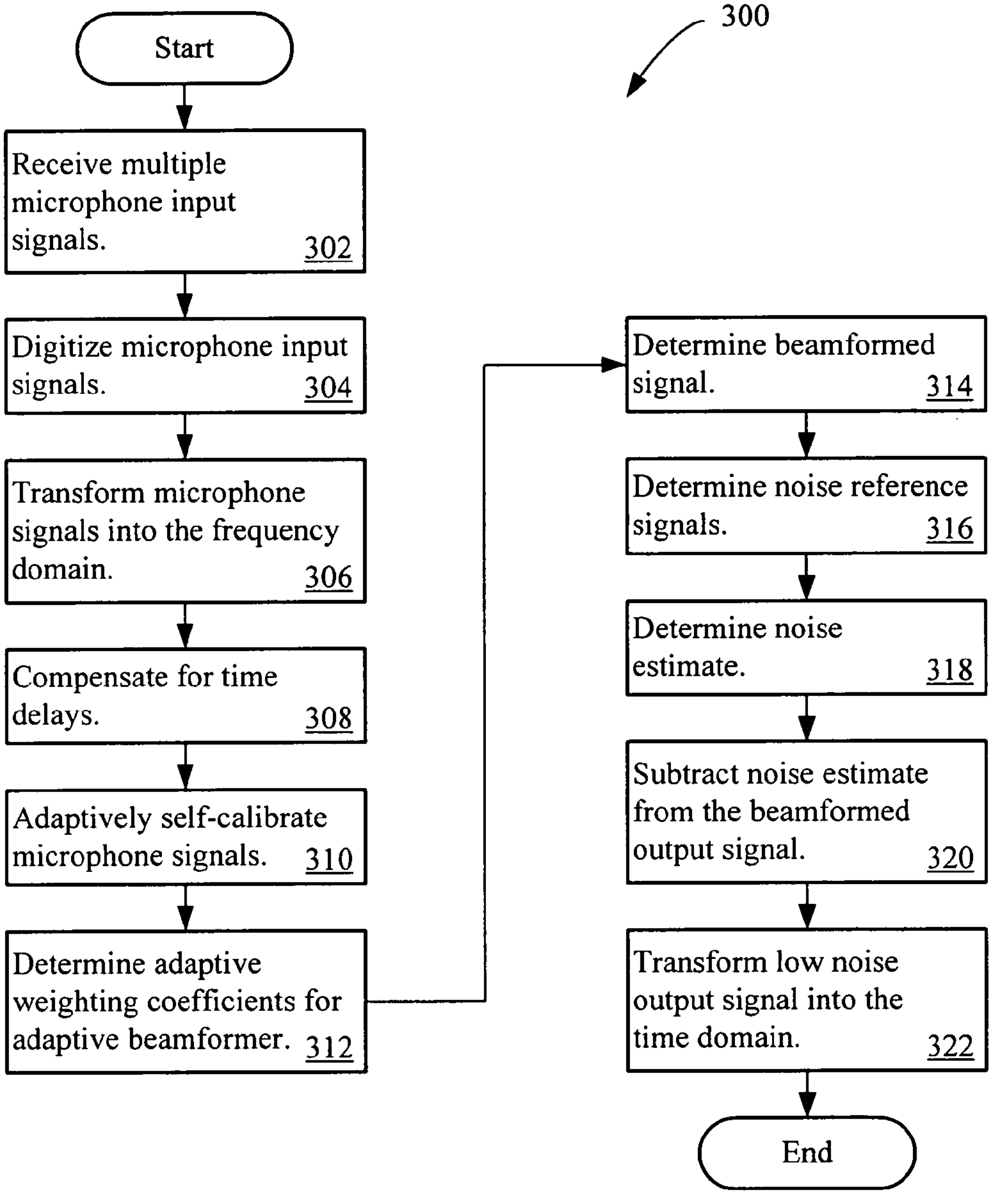
FIG. 3 shows acts which the signal processing system may take to reduce input signal noise.

FIG. 3 shows acts 300 which the multi-channel adaptive speech signal processing systems may take to generate a low noise output signal. The signal processing systems receive multiple microphone input signals (e.g., signals from multiple microphones in a microphone array) (Act 302). An analog to digital converter digitizes the microphone input signals (Act 304) and frequency transform logic (e.g., an FFT) transforms the digitized input signals into the frequency domain (Act 306). The FFT may be a 128-point FFT performed each second, but the FFT length and calculation interval may vary depending on the application in which the signal processing systems 100 and 200 are employed.

The time delay compensation logic 104 compensates for the time delay between microphone signals (Act 308). Additional signal matching (e.g., in phase or amplitude) occurs in the adaptive self-calibration logic 202 (Act 310). The time delay compensation and self-calibration prepare the microphone input signals for processing by the adaptive beamformer 108 and noise reference logic 110.

An adaptive beamformer 108 adaptively determines weights for combining the microphone signals (Act 312). The weights may adapt in response to temporal changes in the noise power, speech amplitude, or other changes in signal characteristics. The adaptive beamformer 108 combines the microphone signals into the beamformed output signal (Act 314).

The noise reference logic 110 generates noise reference signals from the time delay compensated and self-calibrated microphone input signals (Act 316). Noise cancellation logic 118 generates a noise estimate based on the noise reference signals (Act 318). The noise estimate provides an approximation to the residual noise in the beamformed output signal.

The summing logic 122 subtracts the noise estimate from the beamformed signal (Act 320). A low noise output signal results. Frequency to time transformation logic (e.g., an inverse FFT) may convert the low noise output signal to the time domain.

Figure 4:
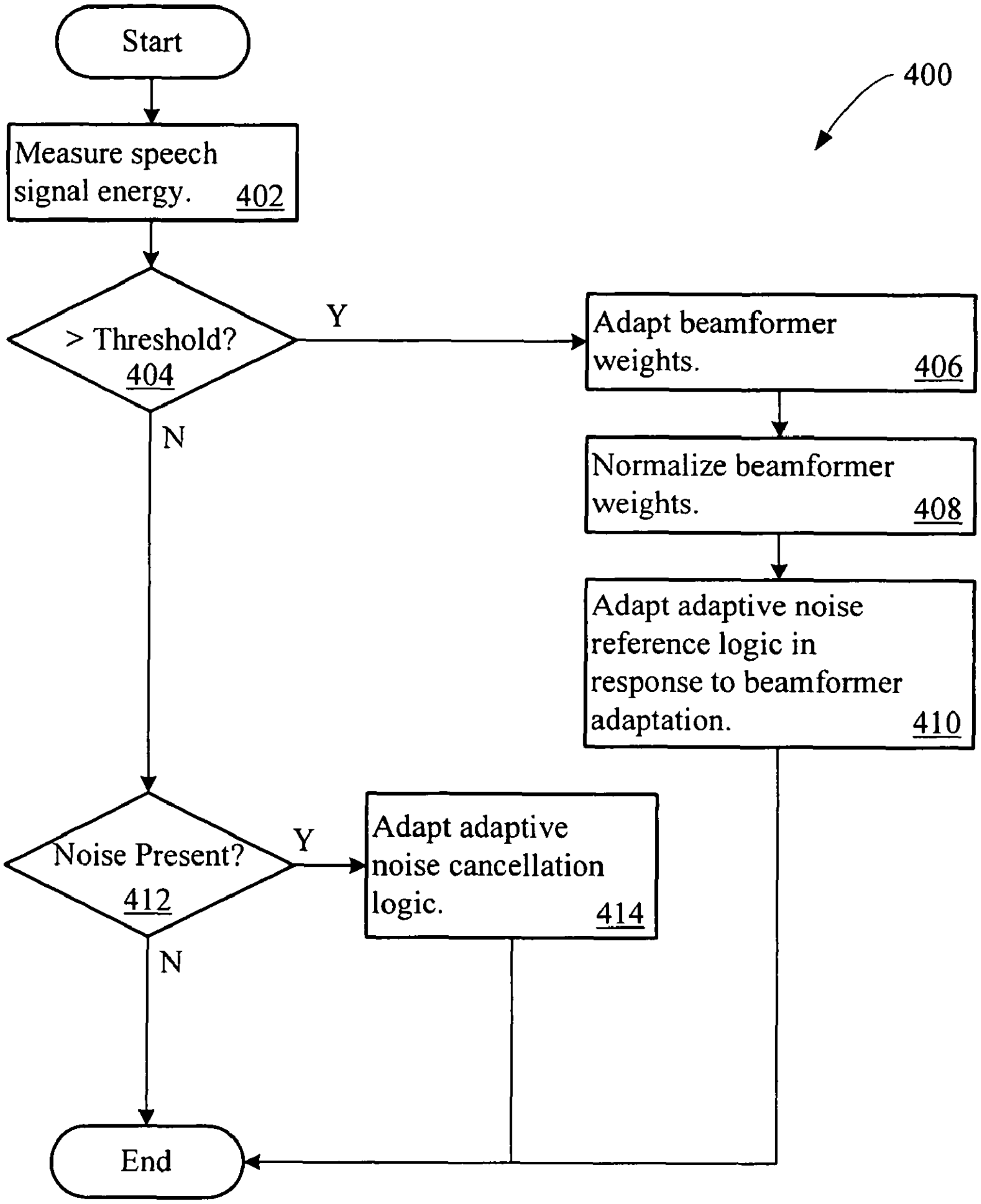
FIG. 4 shows acts which the signal processing system may take to adapt to changing input signal conditions.

FIG. 4 shows acts 400 which the signal processing systems may take to adapt their processing to changing signal conditions. The adaptation control logic 112 measures the signal energy of a desired signal component (e.g., speech) in the microphone signals (Act 402). The adaptation control logic 112 compares the speech signal energy to a threshold energy level (Act 404). If the speech signal energy exceeds the threshold energy level, the adaptation control logic 112 adapts the beamformer weights and controls the adaptation step size based on noise power, speech amplitude, or other signal characteristics (Act 406). The adaptation control logic 112 may also normalize the adapted beamformer weights (Act 408). Adaptation of the beamformer 108 may trigger adaptation of the noise reference logic (Act 410).

If the adaptation control logic 112 does not detect speech signal energy in excess of the threshold noise energy level (Act 404), the adaptation control logic 122 may determine whether the signal contains noise (Act 412). When noise is present, the adaptation control logic 112 adapts the adaptive noise cancellation logic 118 (Act 414).

Figure 5:
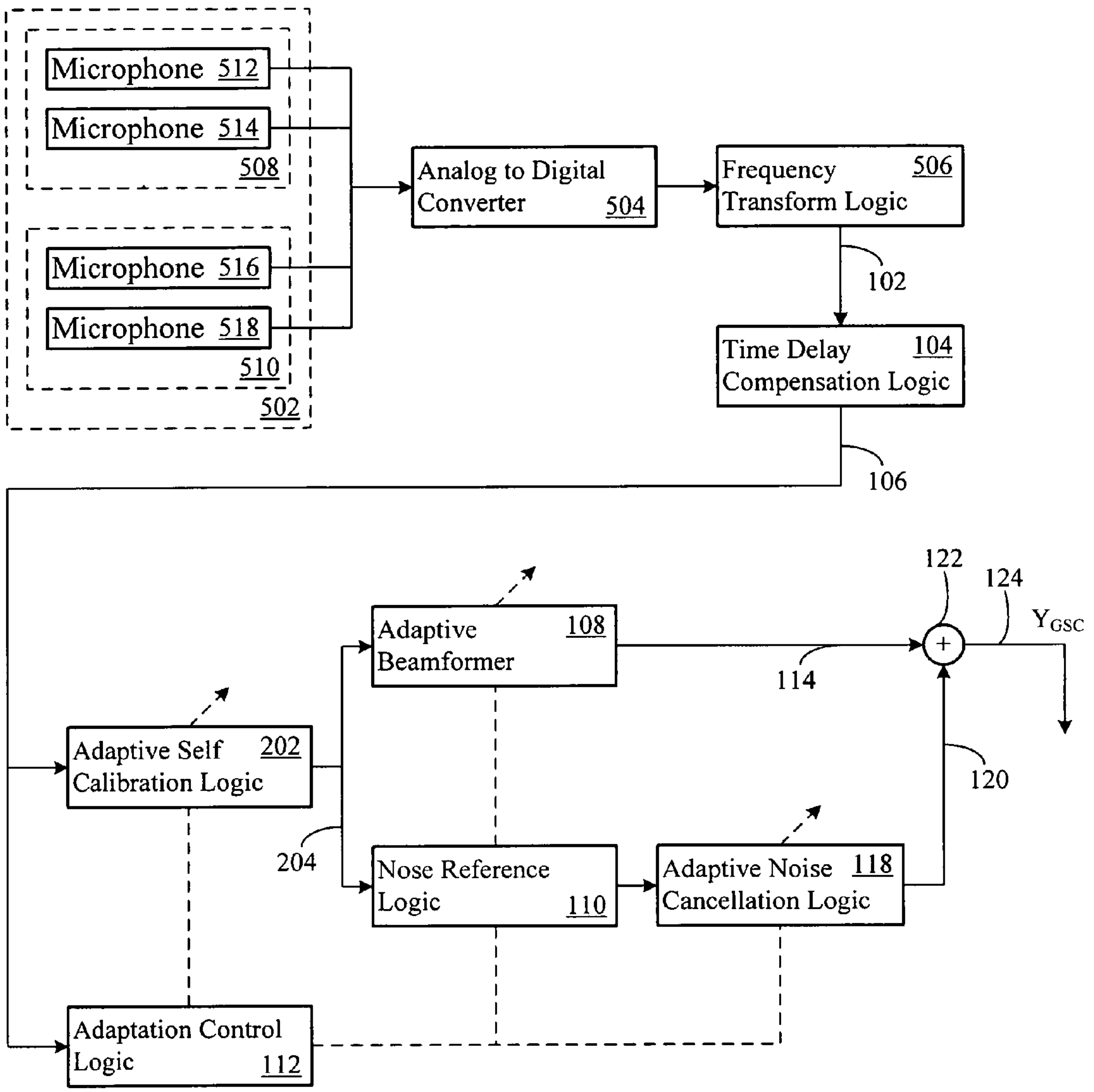
FIG. 5 shows a multi-channel adaptive signal processing system connected to a microphone array.

FIG. 5 shows the multi-channel adaptive signal processing system 200 operating in conjunction with a microphone array 502, analog to digital converter 504, and frequency transform logic 506. The microphone array 502 may include multiple sub-arrays, such as the sub-array 508 and the sub-array 510. Each sub-array may include one or more microphones. In FIG. 5, sub-array 508 includes microphones 512 and 514, while the sub-array 510 includes microphones 516 and 518.

The microphone array 502 outputs microphone signals to the digital to analog converter 504. The analog to digital converter digitizes the microphone signals and the samples are provided to the frequency transform logic 506. The frequency transform logic 506 generates a frequency representation of the microphone input signals for subsequent noise reduction processing.

The microphone array 502 may provide a multi-channel signal transducer for the processing systems 100 and 200. The microphone array 502 may be part of an audio processing system in a car, such as a hands free communication system, voice command system, or other system. The sub-arrays 508 and 510 and/or individual microphones 512-518 may be placed in different locations throughout the car and/or may be oriented in different directions to provide spatially diverse reception of audio signals.

The microphones 512-518 may be placed on or around a rear view mirror, headliner, upper console, or in another location in the vehicle. When two microphones are employed, the first microphone may point toward the driver/or passenger, while the second microphone may point toward the passenger and/or driver. In other implementations, four microphones may be placed on or in the rear view mirror.

Figure 6:
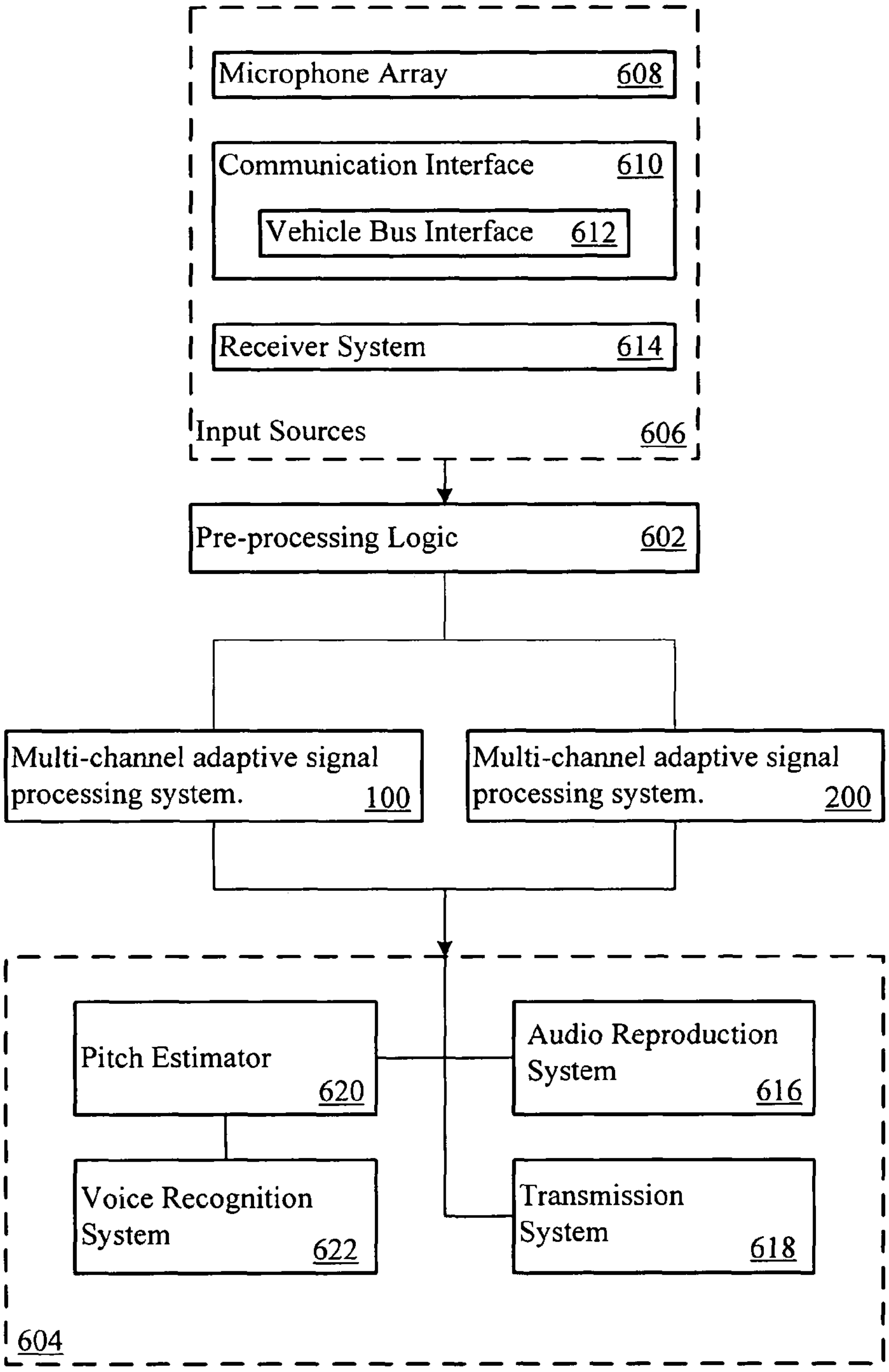
FIG. 6 shows a multi-channel adaptive speech processing system operating in conjunction with pre-processing logic and post-processing logic.

FIG. 6 shows the multi-channel adaptive signal processing systems 100 and/or 200 operating in conjunction with pre-processing logic 602 and post-processing logic 604. The pre-processing logic 602 connects to input sources 606. The signal processing system 100 and 200 may accept input from the input sources 606 directly, or after initial processing by the pre-processing logic 602. The pre-processing logic 602 receives signal data from the input sources 606 and performs any desired signal processing operation (e.g., signal conditioning, filtering, gain control, or other processing) on the signal data prior to processing by the adaptive signal processing systems 100 and 200.

The input sources 606 may include digital or analog signal sources such as a microphone array 608 or other acoustic sensor. The microphone array 608 may include multiple microphones or multiple microphone sub-arrays. The microphone array 608 or any of the microphones in the microphone array 608 may be part of an audio communication system (e.g., an automobile hands-free communication system), speech recognition system (e.g., an automobile voice command system), or any other system. In a vehicle, the microphones may be placed and oriented to provide spatial diversity in the reception of audio energy. The microphones, pre-processing logic 602, and post processing logic 604 may be used in any other application however, including speech recognition or other audio processing applications (e.g., in a speech recognition system for a home or office computer).

Other input sources 606 include a communication interface 610. The communication interface 610 receives digital signal samples (e.g., microphone signal samples) from other systems. The communication interface 610 may be a vehicle bus interface 612 which receives audio data from a sampling system in the vehicle. The sampling system transmits the audio data over the bus to the pre-processing logic 602 and/or adaptive signal processing systems 100 and 200. The receiver system 614 also acts as an input source. The receiver system 614 may be a digital or analog receiver (e.g., a wireless network receiver).

The signal processing systems 100 and/or 200 also connect to post-processing logic 604. The post-processing logic 604 may include an audio reproduction system 616, a digital or analog data transmission system 618, a pitch estimator 620, a voice recognition system 622, or other system. The signal processing systems 100 and 200 may provide a low noise output signal output to any other type of post-processing logic 604.

The voice recognition system 622 may operate in conjunction with the pitch estimator 620. The pitch estimator 620 may include discrete cosine transform circuitry or other processing logic and may process a power or amplitude based representation of the output signal spectrum. The voice recognition system 622 may include circuitry or logic that interprets, takes direction from, initiates actions based on, records, or otherwise processes voice. The voice recognition 622 system may process voice as part of a hands-free device, such as a hands-free cellular phone in an automobile, or may process voice for applications running on a desktop or portable computer system, entertainment device, or any other system. In a hands-free phone, for example, the signal processing systems 100 and 200 provide a low noise, highly intelligible, output signal.

The transmission system 618 may provide a network connection, digital or analog transmitter, or other transmission circuitry or logic. The transmission system 618 may communicate the low noise signal output generated by the signal processing systems 100 and 200 to other devices. In a car phone, for example, the transmission system 618 may communicate low noise signals from the car phone to a base station or other receiver through a wireless connection. The wireless connection may be implemented as a Bluetooth, ZigBee, Mobile-Fi, Ultra-wideband, Wi-fi, WiMax, or other network connection.

The audio reproduction system 616 may include digital to analog converters, filters, amplifiers, and other circuitry or logic. The audio reproduction system 616 may be a speech or music reproduction system. The audio reproduction system 616 may be implemented in a cellular phone, car phone, digital media player/recorder, radio, stereo, portable gaming device, or other device employing sound reproduction.

The adaptive signal processing systems 100 and 200 reduce noise originally present in an input signal. Although noise is greatly reduced, the low noise output signal substantially retains the desired speech signal. Improved speech signal clarity, intelligibility, and understandability result. The low noise output signal enhances performance in a wide range of applications, including speech detection, transmission, and recognition.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

We claim:

1. A noise reduction signal processing system comprising:

multiple microphone signal inputs;

time delay compensation logic coupled to the microphone signal inputs and comprising time delay compensated microphone signal outputs;

adaptive self-calibration logic coupled to the time delay compensation logic, the adaptive self-calibration logic operable to match the phase of time delay compensated microphone signals provided on the time delay compensated microphone signal outputs;

noise reference logic coupled to the adaptive self-calibration logic and comprising noise reference signal outputs;

an adaptive beamformer coupled to the adaptive self-calibration logic and comprising a beamformed signal output, the adaptive beamformer generating a beamformed signal on the beamformed signal output using time-dependent adapted weights; and adaptive noise cancellation logic coupled to the noise reference signal outputs and operable to generate a noise estimate for removing noise from the beamformed signal by subtracting the noise estimate from the beamformed signal, to produce a complex-valued low noise output signal.

2. The noise reduction signal processing system of claim 1, where the adaptive beamformer applies an adaptive real-valued weight to time delay compensated microphone signals provided on the time delay compensated microphone signal outputs.

3. The noise reduction signal processing system of claim 1, where the adaptive beamformer generates the beamformed signal according to:

$$Y_w(n, k) = \sum_{m=1}^{M} A_m(n) X_{T,m}(n, k)$$

where '$Y_w$' is the beamformed signal, 'n' is a frequency bin index, 'k' is a time index, there are 'M' time delay compensated microphone output signals, '$A_m$(n)' is a real-valued time-dependent weight, and '$X_{T,m}$' is a time delay compensated microphone signal output.

4. The noise reduction signal processing system of claim 3, where '$A_m$(n)' is a repeatedly recalculated weight which adapts the adaptive beamformer over time to temporal changes in at least one of noise power and speech amplitude.

5. The noise reduction signal processing system of claim 3, where the repeatedly recalculated weight is a normalized repeatedly recalculated weight.

6. The noise reduction signal processing system of claim 1, where the noise reference logic comprises a blocking matrix.

7. The noise reduction signal processing system of claim 1, wherein the adaptive self-calibration logic coupled to the time delay compensation logic is further operable to match amplitude of time delay compensated microphone signals provided on the time delay compensated microphone signal outputs.

8. The noise reduction signal processing system of claim 1, further comprising adaptation control logic coupled to at least one of the adaptive beamformer and the adaptive noise cancellation logic.

9. The noise reduction signal processing system of claim 8, where the adaptation control logic initiates adaptation depending on at least one of: instantaneous SNR, speech signal detection, speech signal energy level, and acoustic signal direction.

10. The noise reduction signal processing system of claim 1, where the multiple microphone signal inputs comprise a first directional microphone signal input and a second directional microphone signal input from microphones pointing in different directions.

11. The noise reduction signal processing system of claim 1, where the multiple microphone signal input comprise first sub-array microphone signal inputs and second sub-array microphone signal inputs from different microphone sub-arrays.

12. A method for reducing noise comprising:

receiving multiple microphone input signals;

applying a time delay compensation to the microphone input signals, thereby generating time delay compensated microphone output signals;

matching the phase of the time delay compensated microphone output signals, thereby generating calibrated signals;

generating noise reference output signals based on the calibrated signals;

repeatedly updating weights in an adaptive beamformer responsive to temporal changes in the microphone input signals;

beamforming the calibrated signals into a beamformed signal based on the weights;

generating, through use of adaptive noise cancellation, a noise estimate based on the noise reference output signal; and subtracting the noise estimate from the beamformed signal, to produce a complex-valued low noise output signal.

13. The method of claim 12, where repeatedly updating comprises:

repeatedly updating real-valued weights.

14. The method of claim 12, where beamforming comprises determining a beamformed signal according to:

$$Y_w(n, k) = \sum_{m=1}^{M} A_m(n) X_{T,m}(n, k)$$

where '$Y_W$' is the beamformed signal, 'n' is a frequency bin index, 'k' is a time index, there are 'M' time delay compensated microphone output signals, '$A_m$(n)' is a real-valued time-dependent weight, and '$X_{T,m}$ is a time delay compensated microphone signal output.

15. The method of claim 12, further comprising normalizing the weights.

16. The method of claim 12, where generating a noise estimate comprises:

generating a noise estimate using a blocking matrix.

17. The method of claim 12, further comprising applying adaptation control over updating the weights.

18. The method of claim 12, where use of adaptive noise cancellation comprises applying adaptation control over adaptive noise cancellation logic.

19. The method of claim 12, where receiving comprises: receiving a first directional microphone input signal and a second directional microphone signal from microphone pointing in different directions.

20. The method of claim 12, where receiving comprises:

receiving a first microphone input signal and a second microphone input signal from different microphone subarrays.

21. A noise reduction signal processing system comprising:

multiple microphone signal inputs comprising first directional microphone signal inputs and second directional microphone signal inputs from microphones pointing in different directions;

time delay compensation logic coupled to the microphone signal inputs and comprising time delay compensated microphone signal outputs;

adaptive self-calibration logic coupled to the time delay compensation logic, the adaptive self-calibration logic operable to match the phase of time delay compensated microphone output signals on the time delay compensated microphone signal outputs;

an adaptive blocking matrix coupled to the adaptive self-calibration logic and comprising noise reference signal outputs;

an adaptive beamformer coupled to the adaptive self-calibration logic which determines a beamformed signal according to:

$$Y_w(n, k) = \sum_{m=1}^{M} A_m(n) X_{T,m}(n, k)$$

where 'Yw' is the beamformed signal, 'n' is a frequency bin index, 'k' is a time index, there are 'M' time delay compensated microphone output signals, '$A_m$(n)' is a repeatedly adapted real-valued time-dependent weight, and '$X_{T,m}$' is a time delay compensated microphone output signal;

adaptive noise cancellation logic coupled to the noise reference signal outputs and comprising an adaptive noise cancellation output, the adaptive noise cancellation logic operable to generate a noise estimate on the adaptive noise cancellation output; and summing logic for removing noise in the beamformed signal by subtracting the noise estimate from the beamformed signal, to produce a complex-valued low noise output signal.

22. The noise reduction signal processing system of claim 21, where the adaptation control logic initiates adaptation of the adaptive beamformer when speech signal energy exceeds background noise by more than a threshold.

23. The noise reduction signal processing system of claim 21, where the adaptation control logic is also coupled to the adaptive noise cancellation logic, and where the adaptation control logic initiates adaptation of the adaptive noise cancellation logic in the substantial absence of speech signal energy and when noise is present.

24. The noise reduction signal processing system of claim 21, further comprising adaptation control logic coupled to the adaptive beamformer and the adaptive blocking matrix, the adaptation control logic operable to adapt the adaptive blocking matrix in response to adaptation of the adaptive beamformer.

* * * * *